(12) United States Patent
Kita et al.

(10) Patent No.: US 8,563,665 B2
(45) Date of Patent: *Oct. 22, 2013

(54) MODIFIED NAPHTHALENE FORMALDEHYDE RESIN, TRICYCLODECANE SKELETON-CONTAINING NAPHTHOL COMPOUND AND ESTER COMPOUND

(75) Inventors: Seiji Kita, Kurashiki (JP); Masashi Ogiwara, Kurashiki (JP); Mitsuharu Kitamura, Kurashiki (JP); Dai Oguro, Hiratsuka (JP); Gou Higashihara, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 68 days.

This patent is subject to a terminal disclaimer.

(21) Appl. No.: 12/746,611

(22) PCT Filed: Dec. 4, 2008

(86) PCT No.: PCT/JP2008/072003
§ 371 (c)(1),
(2), (4) Date: Sep. 7, 2010

(87) PCT Pub. No.: WO2009/072534
PCT Pub. Date: Jun. 11, 2009

(65) Prior Publication Data
US 2011/0009574 A1    Jan. 13, 2011

(30) Foreign Application Priority Data

Dec. 7, 2007 (JP) .................. 2007-317102
Dec. 10, 2007 (JP) .................. 2007-318874

(51) Int. Cl.
*C08G 14/04* (2006.01)
*C08G 14/12* (2006.01)
*C08G 10/04* (2006.01)

(52) U.S. Cl.
USPC ........................................ 525/472; 528/247

(58) Field of Classification Search
USPC ........................................ 525/472
See application file for complete search history.

(56) References Cited

U.S. PATENT DOCUMENTS

| | | | |
|---|---|---|---|
| 2,330,827 A * | 10/1943 | Kester ............. | 528/160 |
| 2,597,159 A | 5/1952 | May et al. | |
| 3,178,393 A | 4/1965 | Brandt et al. | |
| 3,385,898 A * | 5/1968 | Vanderwerff ........ | 568/437 |
| 3,453,220 A | 7/1969 | Vanderwerff et al. | |
| 4,214,872 A | 7/1980 | Uhrig et al. | |
| 4,395,498 A * | 7/1983 | Benham ............ | 523/158 |
| 5,702,710 A | 12/1997 | Charpentier et al. | |

(Continued)

FOREIGN PATENT DOCUMENTS

| | | |
|---|---|---|
| EP | 1 522 537 A1 | 4/2005 |
| JP | 51 23741 | 2/1976 |

(Continued)

OTHER PUBLICATIONS

U.S. Appl. No. 12/746,421, filed Jun. 4, 2010, Oguro, et al.

(Continued)

*Primary Examiner* — Mike M Dollinger
(74) *Attorney, Agent, or Firm* — Oblon, Spivak, McClelland, Maier & Neustadt, L.L.P.

(57) ABSTRACT

A modified dimethylnaphthalene formaldehyde resin obtained by modifying a polyfunctional dimethylnaphthalene formaldehyde resin having a constituent unit represented by the following general formula [1] in a molecule thereof with at least one member selected from the group consisting of a phenol represented by the following general formula [2], a naphthol represented by the following general formula [3] and a naphthol represented by the following general formula [4], provided that at least any of the naphthol represented by the general formula [3] or the naphthol represented by the general formula [4] must be included

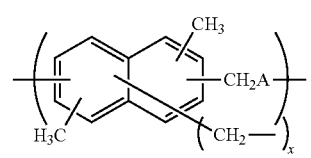

[1]

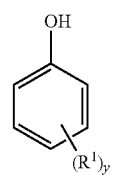

[2]

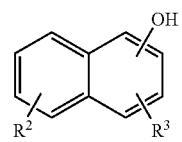

[3]

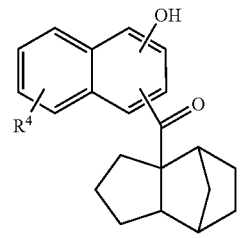

[4]

This resin is excellent in heat resistance and useful for thermosetting resins.

7 Claims, No Drawings

(56) References Cited

U.S. PATENT DOCUMENTS

| | | | |
|---|---|---|---|
| 5,792,826 A * | 8/1998 | Tashima et al. | 528/160 |
| 6,562,996 B2 * | 5/2003 | Saleh | 562/405 |
| 6,713,591 B1 * | 3/2004 | Senzaki et al. | 528/129 |
| 2004/0266976 A1 | 12/2004 | Senzaki et al. | |

FOREIGN PATENT DOCUMENTS

| | | |
|---|---|---|
| JP | 54 86593 | 7/1979 |
| JP | 61 228013 | 10/1986 |
| JP | 63 97615 | 4/1988 |
| JP | 8 225560 | 9/1996 |
| JP | 10298474 A * | 11/1998 |
| JP | 10298477 A * | 11/1998 |
| JP | 11 092543 | 4/1999 |
| JP | 2001 261815 | 9/2001 |
| JP | 2004 091550 | 3/2004 |
| JP | 2006070000 A * | 3/2006 |

OTHER PUBLICATIONS

U.S. Appl. No. 12/743,157, filed May 14, 2010, Kita, et al.
Extended European Search Report issued Feb. 8, 2012 in patent application No. 08858380.2.

* cited by examiner

MODIFIED NAPHTHALENE FORMALDEHYDE RESIN, TRICYCLODECANE SKELETON-CONTAINING NAPHTHOL COMPOUND AND ESTER COMPOUND

TECHNICAL FIELD

The present invention relates to a modified naphthalene formaldehyde resin. Also, the present invention relates to a tricyclodecane skeleton-containing naphthol compound which is used for the production of the modified naphthalene formaldehyde resin and to an ester compound serving as a raw material thereof.

BACKGROUND ART

Modified naphthalene formaldehyde resins can be used for widespread applications such as an electrical insulating material, a resin for resist, a semiconductor sealing resin, an adhesive for printed wiring board, a matrix resin for electrical laminate or prepreg to be mounted in electrical instruments, electronic instruments, industrial instruments, etc., a buildup laminate material, a resin for fiber-reinforced plastic, a sealing resin for liquid crystal display panel, a paint, a variety of coating agents, an adhesive and the like.

An aromatic hydrocarbon resin obtained by allowing a polycyclic aromatic hydrocarbon composed mainly of a monomethylnaphthalene and/or a dimethylnaphthalene and paraformaldehyde to react with each other in the presence of an aromatic monosulfonic acid is known, and the obtained resin is excellent in compatibility with a liquid epoxy resin and solubility in xylene (see Patent Document 1).

Also, there is known a method for obtaining a phenol resin having a structure in which naphthalene and a phenolic hydroxyl group-containing compound are bonded via a methylene group through a reaction between a methoxymethylene naphthalene compound and a phenolic hydroxyl group-containing compound such as phenol, cresol, naphthol, etc. in the presence of diethyl sulfate (see Patent Document 2).

Now, in order to use a resin obtained through a condensation reaction of a polycyclic aromatic hydrocarbon formaldehyde resin and a phenolic hydroxyl group-containing compound for a thermosetting resin application, it is more preferable that the obtained resin is polyfunctional.

However, in the case where naphthalene or a monomethylnaphthalene is used as a raw material of resin, it is difficult to obtain a polyfunctional resin by a usual method so that it was necessary to perform a special reaction such as an interface reaction (see Patent Documents 2 and 3).

[Patent Document 1] JP-A-54-86593
[Patent Document 2] JP-A-2004-91550
[Patent Document 3] JP-A-61-228013
[Patent Document 4] JP-A-11-92543

DISCLOSURE OF THE INVENTION

Problems that the Invention is to Solve

Furthermore, according to investigations made by the present inventors, in addition to naphthalene and a monomethylnaphthalene, even when a dimethylnaphthalene is used as a raw material, there may be the case where a polyfunctional resin is not obtained, and it has become clear that in order to obtain a polyfunctional resin serving as a raw material, selection of the kind of the dimethylnaphthalene is important.

An object of the present invention is to provide a modified dimethylnaphthalene formaldehyde resin with high heat resistance which is useful for a thermosetting resin application, the modified dimethylnaphthalene formaldehyde resin being obtained by using, as a raw material, a dimethylnaphthalene formaldehyde resin which is polyfunctional and rich in reactivity and modifying the dimethylnaphthalene formaldehyde resin with a naphthol or a naphthol and a phenol. Furthermore, another object of the present invention is to provide a tricyclodecane skeleton-containing naphthol compound capable of being used for the modification of a dimethylnaphthalene formaldehyde resin and an ester compound serving as a raw material thereof.

Means for Solving the Problems

The present inventors made extensive and intensive investigations. As a result, it has been found that the foregoing objects can be attained by obtaining a modified dimethylnaphthalene formaldehyde resin using a polyfunctional dimethylnaphthalene formaldehyde resin which is obtained by using a dimethylnaphthalene having one methyl group on each of two benzene rings in a naphthalene ring thereof and allowing this to react with formaldehyde, leading to the present invention.

That is, the present invention is concerned with:

(1) A modified dimethylnaphthalene formaldehyde resin obtained by modifying a polyfunctional dimethylnaphthalene formaldehyde resin having a constituent unit represented by the following general formula [1] in a molecule thereof with at least one member selected from the group consisting of a phenol represented by the following general formula [2], a naphthol represented by the following general formula [3] and a naphthol represented by the following general formula [4] (provided that at least any of the naphthol represented by the general formula [3] or the naphthol represented by the general formula [4] is included):

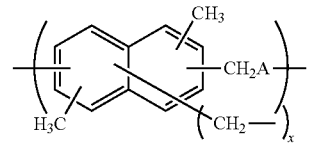

[1]

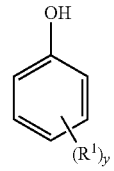

[2]

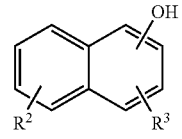

[3]

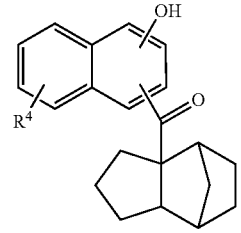

[4]

wherein $R^1$ represents an alkyl group having from 1 to 4 carbon atoms; each of $R^2$, $R^3$ and $R^4$ independently represents a hydrogen atom or an alkyl group having from 1 to 3 carbon atoms; A is represented by —(OCH$_2$)$_t$—; t is from 0 to 2; x is from 0 to 4; and y represents an integer of from 0 to 2;

(2) The modified dimethylnaphthalene formaldehyde resin as set forth above in (1), wherein in the polyfunctional dimethylnaphthalene formaldehyde resin having a constituent unit represented by the general formula [1] in a molecule thereof, a mean value of the number of hydrogen atoms substituted by a reaction for producing the dimethylnaphthalene formaldehyde resin among the six hydrogen atoms directly bonded on the naphthalene ring is from 1.5 to 3.5;

(3) The modified dimethylnaphthalene formaldehyde resin as set forth above in (1) or (2), wherein a dimethylnaphthalene which is a raw material of the polyfunctional dimethylnaphthalene formaldehyde resin having a constituent unit represented by the general formula [1] in a molecule thereof is at least one member selected from the group consisting of 1,5-dimethylnaphthalene, 1,6-dimethylnaphthalene, 2,6-dimethylnaphthalene, 1,7-dimethylnaphthalene, 1,8-dimethylnaphthalene and 2,7-dimethylnaphthalene;

(4) The modified dimethylnaphthalene formaldehyde resin as set forth above in (3), wherein the dimethylnaphthalene is a dimethylnaphthalene obtained through a chemical synthesis using, as starting raw materials, o-xylene and 1,3-butadiene, or p-xylene and 1,3-butadiene;

(5) The modified dimethylnaphthalene formaldehyde resin as set forth above in any one of (1) to (4), wherein the phenol represented by the general formula [2] is at least one member selected from the group consisting of phenol, cresol, 4-t-butylphenol and xylenol;

(6) The modified dimethylnaphthalene formaldehyde resin as set forth above in any one of (1) to (5), wherein the naphthol represented by the general formula [3] is 1-naphthol and/or 2-naphthol;

(7) The modified dimethylnaphthalene formaldehyde resin as set forth above in any one of (1) to (6), wherein the naphthol represented by the general formula [4] is the following compound:

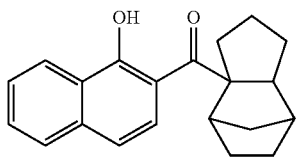

(8) The modified dimethylnaphthalene formaldehyde resin as set forth above in any one of (1) to (7), having a weight average molecular weight (Mw) of from 500 to 5,000;

(9) A method for producing a tricyclodecane skeleton-containing naphthol compound represented by the following formula (1):

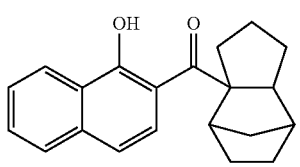

including a step of subjecting an ester compound represented by the following formula (2):

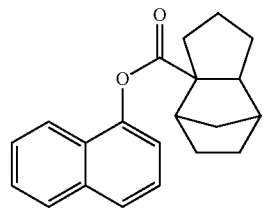

to a Fries rearrangement reaction;

(10) A tricyclodecane skeleton-containing naphthol compound represented by the following formula (1):

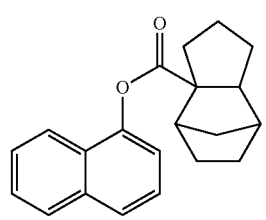

(11) A method for producing an ester compound represented by the following formula (2):

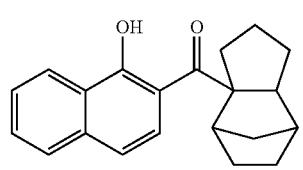 [SMILES: O=C(c1ccc2ccccc2c1O)C12CCCC1C1CCC2C1]

including a step of allowing tricyclo[5.2.1.0$^{2,6}$]deca-3-ene and carbon monoxide to react with each other in the presence of hydrogen fluoride at from 20 to 40° C. to obtain an acyl fluoride represented by the following formula (3):

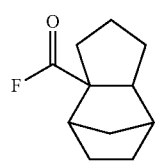

and subjecting the obtained acyl fluoride to an esterification reaction with 1-naphthol at not higher than 20° C.; and

(12) An ester compound represented by the following formula (2):

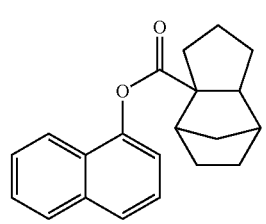

Advantages of the Invention

The modified dimethylnaphthalene formaldehyde resin of the present invention is excellent in heat resistance and useful for thermosetting resins which are used for an electrical insulating material, a resin for resist, a semiconductor sealing resin, an adhesive for printed wiring board, a matrix resin for electrical laminate or prepreg to be mounted in electrical instruments, electronic instruments, industrial instruments, etc., a buildup laminate material, a resin for fiber-reinforced plastic, a sealing resin for liquid crystal display panel, a paint, a variety of coating agents, an adhesive, a laminate for electrical or electronic parts, a molded article, a coating material, a sealing material and the like. Also, the tricyclodecane skeleton-containing naphthol compound represented by the foregoing formula (1) is useful as a variety of industrial chemical raw materials and a variety of raw materials for producing an optical functional material or an electronic functional material.

Best Modes for Carrying Out the Invention

As described previously, the present invention is concerned with a modified dimethylnaphthalene formaldehyde resin (hereinafter sometimes abbreviated as "modified resin") which is obtained by modifying a polyfunctional dimethylnaphthalene formaldehyde resin having a constituent unit represented by the following general formula [1] in a molecule thereof:

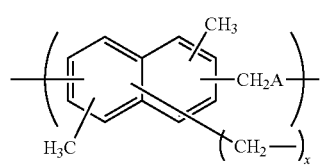

[1]

with at least one member selected from the group consisting of a phenol represented by the following general formula [2], a naphthol represented by the following general formula [3] and a naphthol represented by the following general formula [4]:

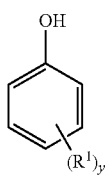

[2]

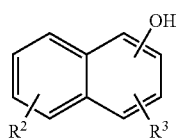

[3]

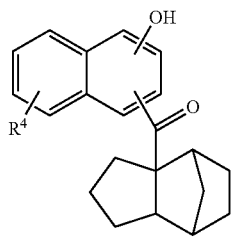

[4]

provided that
at least any of the naphthol represented by the general formula [3] or the naphthol represented by the general formula [4] is included.

Here, the "polyfunctionality" of the polyfunctional dimethylnaphthalene formaldehyde resin as referred to in the present specification means that a mean value of the number of hydrogen atoms substituted by a reaction for producing a dimethylnaphthalene formaldehyde resin among the six hydrogen atoms directly bonded on the naphthalene ring in the dimethylnaphthalene (hereinafter sometimes referred to as "mean value of the number of substituted hydrogen atoms per one naphthalene ring in the dimethylnaphthalene formaldehyde resin") exceeds 1.5. In measuring the obtained resin by means of $^1$H-NMR, the number of substituted hydrogen atoms is a numerical value calculated utilizing an integrated value of methyl protons in the vicinity of from 2.3 to 3.2 ppm and an integrated value of protons directly bonded on the aromatic ring in the vicinity of from 6.8 to 8.2 ppm.

<Polyfunctional Dimethylnaphthalene Formaldehyde Resin>

The polyfunctional dimethylnaphthalene formaldehyde resin is obtained through a condensation reaction between a dimethylnaphthalene having one methyl group on each of two benzene rings in a naphthalene ring thereof and formaldehyde.

(Dimethylnaphthalene)

The dimethylnaphthalene as a raw material of the polyfunctional dimethylnaphthalene formaldehyde resin is obtained through a chemical synthesis using, as starting raw materials, o-xylene and 1,3-butadiene, or p-xylene and 1,3-butadiene. Specifically, the dimethylnaphthalene which is used in the present invention is at least one member selected from the group consisting of 1,5-dimethylnaphthalene, 1,6-dimethylnaphthalene, 2,6-dimethylnaphthalene, 1,7-dimethylnaphthalene, 1,8-dimethylnaphthalene and 2,7-dimethylnaphthalene.

The dimethylnaphthalene of at least one member selected from the group consisting of 1,5-dimethylnaphthalene, 1,6-dimethylnaphthalene and 2,6-dimethylnaphthalene can be obtained by allowing o-xylene and 1,3-butadiene to react with each other in the presence of a strong alkali catalyst to form o-toluoyl-1-pentene (step A), subsequently cyclizing the o-toluoyl-1-pentene to obtain a tetralin compound (step B) and dehydrogenating the tetralin compound to obtain a naphthalene compound (step C) and optionally, isomerizing the naphthalene compound to obtain a structural isomer (step D), followed by separation and purification by means of distillation, crystallization or the like, if necessary.

Also, the dimethylnaphthalene of at least one member selected from the group consisting of 1,7-dimethylnaphthalene, 1,8-dimethylnaphthalene and 2,7-dimethylnaphthalene can be obtained by allowing p-xylene and 1,3-butadiene as starting raw materials to react with each other according to the foregoing steps A to C and optionally, the step D, followed by separation and purification by means of distillation, crystallization or the like, if necessary.

As the foregoing steps A to D, known methods, for example, a method disclosed in JP-A-2006-70000 can be utilized.

In this way, by producing the dimethylnaphthalene formaldehyde resin using the dimethylnaphthalene obtained through a chemical synthesis using a xylene (o-xylene or p-xylene) and 1,3-butadiene as starting raw materials in a process including the foregoing steps A to C and optionally, the step D, it is possible to obtain a polyfunctional dimethylnaphthalene formaldehyde resin which is polyfunctional and rich in reactivity and in which a content of each of a sulfur atom and a nitrogen atom in the resin is not more than 0.5 ppm.

It is important that the raw material dimethylnaphthalene which is used in the present invention is a dimethylnaphthalene having one methyl group on each of two benzene rings in a naphthalene ring thereof. As a result of extensive and intensive investigations made by the present inventors, it has become clear that in the case of using, as a raw material, an unsubstituted compound; a monomethylnaphthalene such as 1-methylnaphthalene, etc.; and at least one dimethylnaphthalene selected from the group consisting of 1,2-dimethylnaphthalene, 1,3-dimethylnaphthalene, 1,4-dimethylnaphthalene and 2,3-dimethylnaphthalene each having two methyl groups substituted only on a benzene ring of one side of a naphthalene ring thereof, a polyfunctional naphthalene formaldehyde resin is not obtainable unless a special reaction mode such as an interface reaction is adopted. Also, in the case of using a naphthalene compound having three or more methyl groups substituted thereon, the number of reactive points with formaldehyde (the number of hydrogen atoms directly bonded on the naphthalene ring) becomes small so that a polyfunctional naphthalene formaldehyde resin could not be obtained.

The mean value of the number of substituted hydrogen atoms per one naphthalene ring in the polyfunctional dimethylnaphthalene formaldehyde resin is from 1.5 to 3.5, preferably from 1.8 to 3.5, more preferably from 2.0 to 3.5, further preferably from 2.0 to 3.3, and especially preferably from 2.5 to 3.0. What the mean value of the number of substituted hydrogen atoms per one naphthalene ring in the resin is less than 1.5 is not preferable because an active group (for example, a methylol group, a methoxymethyl group, etc.) which is rich in reactivity with a third component becomes few so that there is a concern that an acquisition amount of a modified resin obtained by a reaction with the third component is small. In particular, what the mean value of the number of substituted hydrogen atoms is 2.0 or more is preferable because the reactivity with the third component is sufficient. On the other hand, what the mean value of the number of substituted hydrogen atoms per one naphthalene ring in the resin exceeds 3.5 is technically difficult.

Since the polyfunctional dimethylnaphthalene formaldehyde resin has high reactivity with a phenol, a carboxylic acid, a polyol, etc. each having active hydrogen.

(Formaldehyde)

As the formaldehyde, compounds capable of generating formaldehyde, such as formalin, paraformaldehyde, trioxan, etc., all of which are industrially easily available, and the like can be exemplified. In performing a condensation reaction, a molar ratio of the dimethylnaphthalene to formaldehyde is from 1/1 to 1/6, preferably from 1/1.5 to 1/6, more preferably 1/2 to 1/6, further preferably from 1/2.5 to 1/6, and especially preferably from 1/2.5 to 1/5. When the molar ratio of the dimethylnaphthalene to formaldehyde is made to fall within the foregoing range, not only a resin yield of the obtained dimethylnaphthalene formaldehyde resin can be kept relatively high, but an amount of unreacted residual formaldehyde can be made small.

(Production Method of Polyfunctional Dimethylnaphthalene Formaldehyde Resin)

The condensation reaction of the foregoing dimethylnaphthalene compound and the foregoing formaldehyde is carried out in the presence of water and an acid catalyst.

As the acid catalyst, sulfuric acid, p-toluenesulfonic acid and the like are exemplified, but in general, sulfuric acid is suitable. For example, in the case of using sulfuric acid, a use amount of the acid catalyst is adjusted such that a concentration of sulfuric acid in a component composed of formaldehyde, water and sulfuric acid is preferably from 20 to 55% by mass, and more preferably from 25 to 40% by mass. When the concentration of sulfuric acid is made to fall within this range, an appropriate reaction rate is obtainable, and furthermore, it is possible to prevent an increase of the viscosity of the resin to be caused due to a fast reaction rate. On the other hand, in the case of using p-toluenesulfonic acid, it is preferable to use p-toluenesulfonic acid so as to adjust its concentration slightly higher than that in the case of using sulfuric acid, for example, a concentration of paraformaldehyde in a component composed of formaldehyde, water and paraformaldehyde is adjusted at from 35 to 60% by mass.

Also, a concentration of formaldehyde in a component composed of formaldehyde, water and sulfuric acid in the raw material components is preferably from 20 to 40% by mass. By setting the concentration of formaldehyde to be from 20 to 40% by mass, a reaction rate which is preferable for practical use is obtainable.

The condensation reaction of the naphthalene compound and formaldehyde is usually carried out at atmospheric pressure and carried out while refluxing upon heating at 100° C. as a boiling point of water. However, a reaction temperature may be properly chosen within the range of from ordinary temperature to 100° C., and a reaction pressure may be an elevated pressure of from about 0.001 to 0.02 MPa (gauge pressure). In the case of using, as a raw material, a dimethylnaphthalene having a melting point of 100° C. or higher, for the purpose of setting the reaction temperature to be its melting point or higher, it is preferable that the reaction is carried out under an elevated pressure of from about 0.01 to 0.02 MPa (gauge pressure). Also, if desired, a solvent which is inert to the condensation reaction can be used. Examples of the solvent include an aromatic hydrocarbon such as ethylbenzene, etc.; a saturated aliphatic hydrocarbon such as heptane, hexane, etc.; an alicyclic hydrocarbon such as cyclohexane, etc.; a ketone such as methyl isobutyl ketone, etc.; an ether such as dioxane, dibutyl ether, etc.; an alcohol such as 2-propanol, etc.; a carboxylic acid ester such as ethyl propionate, etc.; a carboxylic acid such as acetic acid, etc.; and the like.

In general, a reaction time is preferably from about 4 to 10 hours, and more preferably from 5 to 8 hours. By adopting such a reaction time, the dimethylnaphthalene formaldehyde resin having desired properties is obtainable economically and industrially advantageously.

Also, if desired, the present condensation reaction may be carried out while heat refluxing by the addition of an aliphatic lower alcohol such as methanol, ethanol, isopropanol, etc. By performing the reaction by the addition of an aliphatic lower alcohol, the aliphatic lower alcohol is captured as a terminal group of the dimethylnaphthalene formaldehyde resin, namely a methylol group directly bonded on the naphthalene ring of the repeating unit structure is partially captured as an alkoxy group, thereby enabling one to realize a low molecular weight and to decrease the viscosity.

After the condensation reaction, if desired, by after further adding the foregoing solvent for dilution, allowing the mixture to stand to cause two-phase separation, separating a resin phase as an oily phase from an aqueous phase, further washing it with water, thereby completely removing the acid catalyst and then removing the added solvent and the unreacted raw material dimethylnaphthalene by a general method such as distillation, etc., a polyfunctional dimethylnaphthalene formaldehyde resin having desired properties is obtainable.

(Characteristic Values of Polyfunctional Dimethylnaphthalene Formaldehyde Resin)

A weight average molecular weight (Mw) of the thus obtained polyfunctional dimethylnaphthalene formaldehyde resin is preferably from 300 to 1,500, more preferably from 500 to 1,300, and further preferably from 800 to 1,200; and a degree of dispersion (Mw/Mn) is preferably from 1.5 to 3, and more preferably from 1.5 to 2.3. Also, each of a content of a sulfur atom and a content of a nitrogen atom in the polyfunctional dimethylnaphthalene formaldehyde resin is not more than 0.5 ppm.

Also, it is possible to modify the thus obtained polyfunctional dimethylnaphthalene formaldehyde resin with a naphthol or the like in the following manners.

In the general formula [1], A is represented by —(OCH$_2$)$_t$—; and t is from 0 to 2. Also, x is from 0 to 4, preferably from 0 to 2, and more preferably from 0 to 1.

<Modified Dimethylnaphthalene Formaldehyde Resin>

The modified dimethylnaphthalene formaldehyde resin having been modified with a naphthol, or a naphthol and a phenol according to the present invention is obtained by adding the foregoing naphthol having a phenolic hydroxyl group and optionally the foregoing phenol to the foregoing polyfunctional dimethylnaphthalene formaldehyde resin and subjecting the mixture to a condensation reaction upon heating in the presence of an acid catalyst. The naphthol is represented by the foregoing general formula [3] or [4]; and the phenol is represented by the foregoing general formula [2].

In the foregoing general formula [3], each of $R^2$ and $R^3$ independently represents a hydrogen atom or an alkyl group having from 1 to 3 carbon atoms. Examples of the alkyl group include a methyl group, an ethyl group, an n-propyl group and an isopropyl group. Each of $R^2$ and $R^3$ is preferably a hydrogen atom.

In the foregoing general formula [4], $R^4$ represents a hydrogen atom or an alkyl group having from 1 to 3 carbon atoms. Examples of the alkyl group include a methyl group, an ethyl group, an n-propyl group and an isopropyl group. $R^4$ is preferably a hydrogen atom.

The naphthol is preferably 1-naphthol, 2-naphthol or a tricyclodecane skeleton-containing naphthol compound represented by the following formula (1) or (4), and from the viewpoint of heat resistance, a tricyclodecane skeleton-containing naphthol compound represented by the formula (1) is more preferable. The naphthol may be used singly or in combinations with two or more kinds thereof.

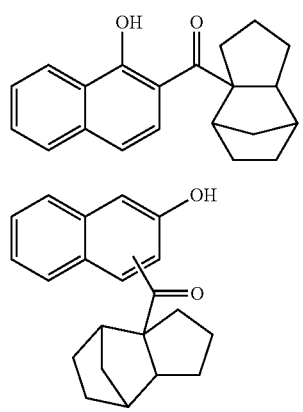

In modifying the polyfunctional dimethylnaphthalene formaldehyde resin, from the viewpoint of heat resistance, the use of the naphthol is essential. In any of the naphthol represented by the foregoing general formula [3] and the naphthol represented by the foregoing general formula [4], a use amount of the naphthol is preferably from 10 to 150 parts by mass, more preferably from 20 to 120 parts by mass, and further preferably from 30 to 100 parts by mass, and from the viewpoint of heat resistance, especially preferably from 40 to 90 parts by mass based on 100 parts of the polyfunctional dimethylnaphthalene formaldehyde resin. Also, in the case of jointly using the naphthol represented by the foregoing general formula [3] and the naphthol represented by the foregoing general formula [4], a total use amount thereof is preferably from 10 to 150 parts by mass, more preferably from 20 to 120 parts by mass, and further preferably from 30 to 100 parts by mass, and from the viewpoint of heat resistance, especially preferably from 40 to 90 parts by mass based on 100 parts by mass of the polyfunctional dimethylnaphthalene formaldehyde resin.

Also, in the foregoing general formula [2], $R^1$ represents an alkyl group having from 1 to 4 carbon atoms. Examples of the alkyl group include a methyl group, an ethyl group, an n-propyl group, an isopropyl group, an n-butyl group, an isobutyl group, an s-butyl group and a t-butyl group.

y is from 0 to 2, and preferably 0 or 1.

It is preferable to use at least one member selected from the group consisting of phenol, cresol, 4-t-butylphenol, xylenol and propionylphenol as the phenol.

In modifying the polyfunctional dimethylnaphthalene formaldehyde resin, if desired, the heat resistance can also be adjusted by using the phenol along with the naphthol. In that case, a use amount of the phenol is preferably not more than 80 parts by mass, more preferably not more than 40 parts by mass, and further preferably not more than 10 parts by mass based on 100 parts by mass of the polyfunctional dimethylnaphthalene formaldehyde resin, and for the purpose of enhancing the heat resistance of the modified resin, it is especially preferable that the phenol is not used.

The condensation reaction of the polyfunctional dimethylnaphthalene formaldehyde resin and the foregoing naphthol and the foregoing phenol is generally carried out at atmospheric pressure and carried out while refluxing upon heating at a melting point of each of the polyfunctional dimethylnaphthalene formaldehyde resin, the naphthol and the phenol or higher (usually from 130 to 250° C.). Also, if desired, the condensation reaction can be carried out under an elevated pressure. Furthermore, if desired, a solvent which is inert to the condensation reaction can be used. Examples of the solvent include an aromatic hydrocarbon such as ethylbenzene, etc.; a saturated aliphatic hydrocarbon such as heptane, hexane, etc.; an alicyclic hydrocarbon such as cyclohexane, etc.; a ketone such as methyl isobutyl ketone, etc.; an ether such as dioxane, dibutyl ether, etc.; an alcohol such as 2-propanol, etc.; a carboxylic acid ester such as ethyl propionate, etc.; a carboxylic acid such as acetic acid, etc.; and the like.

Examples of the acid catalyst which can be used for the condensation reaction include sulfuric acid, p-toluenesulfonic acid, etc. Of these, p-toluenesulfonic acid is preferable. In the case of using p-toluenesulfonic acid, a use amount of the acid catalyst is adjusted such that a concentration of p-toluenesulfonic acid in a component composed of the polyfunctional dimethylnaphthalene aldehyde resin, the naphthol and p-toluenesulfonic acid is preferably from 0.0001 to 0.5% by mass, more preferably from 0.01 to 0.5 by mass, and further preferably from 0.05 to 0.4% by mass. When the concentration of p-toluenesulfonic acid is made to fall within the foregoing range, an appropriate reaction rate is obtainable, and it is possible to prevent an increase of the viscosity of the resin to be caused due to a large reaction rate.

A reaction time is preferably from about 1 to 10 hours, and more preferably from about 2 to 6 hours. When the reaction time falls within this range, a modified resin having desired properties is obtainable economically and industrially advantageously.

After completion of the reaction, if desired, by after further adding the foregoing solvent for dilution, allowing the mixture to stand to cause two-phase separation, separating a resin phase as an oily phase from an aqueous phase, further washing the resin phase with water, thereby completely removing the acid catalyst and then removing the added solvent and the unreacted naphthol by a general method such as distillation, etc., a modified resin is obtainable.

(Characteristic Values of Modified Resin)

Though a hydroxyl group value (mg-KOH/g) of the thus obtained modified resin of the present invention is not particularly limited, it is preferably from 10 to 500, more preferably from 10 to 400, and further preferably from 10 to 300.

Also, though a weight average molecular weight (Mw) of the thus obtained modified resin of the present invention is not particularly limited, it is preferably from 500 to 5,000, more preferably from 1,000 to 5,000, and further preferably from 1,500 to 5,000; and a degree of dispersion (Mw/Mn) is preferably from 1.5 to 6, more preferably from 1.5 to 5, and further preferably from 1.8 to 3.5.

<Production Method of Naphthol>

A production method of the naphthol represented by the general formula [4] is hereunder described.

For the sake of convenience, though an example of a production method of a tricyclodecane skeleton-containing naphthol compound represented by the following formula (1):

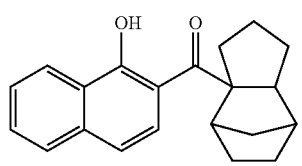

(hereinafter abbreviated as "naphthol compound (1)") is exemplified, other naphthol compounds in which the position of the substituent is different can be produced in the same method.

The foregoing naphthol compound (1) can be produced through the following three stages.

(First Stage)

Production of acyl fluoride represented by the following formula (3):

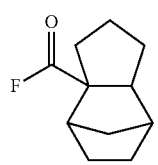

(hereinafter referred to as "acyl fluoride (3)") by means of a carbonylation reaction of tricyclo[5.2.1.0$^{2,6}$]deca-3-ene (hereinafter abbreviated as "DHDCPD")

(Second Stage)

Production of an ester compound represented by the following formula (2):

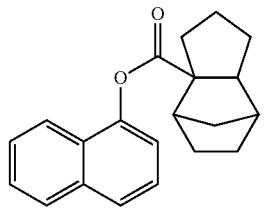

(hereinafter referred to as "ester compound (2)") by means of an esterification reaction between the foregoing acyl fluoride (3) and 1-naphthol (Third Stage)

Production of the naphthol compound (1) by means of the Fries rearrangement of the foregoing ester compound (2)

(First Stage: Production of the Acyl Fluoride (3))

A carbonylation reaction solution containing the acyl fluoride (3) is obtained by allowing DHDCPD to react in the presence of hydrogen fluoride (hereinafter abbreviated as "HF") under an elevated pressure with carbon monoxide. On that occasion, an inert gas such as nitrogen, methane, etc. may be contained in carbon monoxide.

Though a partial pressure of carbon monoxide is not particularly limited, in general, it is from about 0.5 to 5 MPa, and more preferably from 1 to 3 MPa. When the partial pressure of carbon monoxide falls within the foregoing range, the carbonylation reaction is sufficiently advanced, a side reaction such as disproportionation, polymerization, etc. is suppressed, and large expenditure on plant and equipment is not required. Also, a reaction temperature is usually from 10 to 60° C., and from the viewpoint of yield, it is preferably from 20 to 40° C., and more preferably from 25 to 35° C. The highest yield is obtained in the vicinity of 30° C.

HF is preferably a substantially anhydrous material.

From the viewpoint that not only the carbonylation reaction is sufficiently advanced, but a side reaction such as disproportionation, polymerization, etc. is suppressed and also from the viewpoints of expenses for separating HF, volume efficiency of a reaction apparatus and the like, a use amount of HF is preferably from 1 to 30 molar times, more preferably from 4 to 12 molar times, and further preferably from 6 to 10 molar times relative to the DHDCPD.

(Second Stage: Production of the Ester Compound (2))

Though after removing HF from the carbonylation reaction solution containing the acyl fluoride (3) obtained in the first stage, the residue may be allowed to react with 1-naphtol, HF acts as a catalyst in the esterification reaction, and therefore, it is preferable that the carbonylation reaction solution is mixed with 1-naphthol as it is without separating HF therefrom and allowed to react with each other, thereby obtaining an esterification reaction solution containing the ester compound (2).

A reaction temperature is not higher than 20° C., and from the viewpoints of suppressing decomposition of the formed ester, suppressing by-production of water due to a dehydration reaction of the added alcohol and the like, the reaction temperature is preferably from −40 to 20° C., more preferably from −20 to 10° C., and further preferably from −10 to 10° C. Though there may be the case where the Fries rearrangement of the third stage as described later is advanced depending upon the reaction temperature, there is not particularly caused a problem.

As a standard, a use amount of 1-naphthol is preferably from 0.1 to 3 molar times, more preferably from 0.3 to 2 molar times, and further preferably from 0.3 to 0.8 molar times relative to the DHDCPD used in the first stage.

(Third Stage: Tricyclodecane Skeleton-Containing Naphthol Compound)

By elevating a temperature of the esterification reaction solution containing the ester compound (2) obtained in the second stage, the Fries rearrangement of the ester compound (2) is advanced, thereby forming the naphthol compound (1). In this rearrangement reaction, HF acts as a catalyst, too.

A reaction temperature is preferably from −10 to 40° C., more preferably from −10 to 30° C., further preferably from −10 to 25° C., and especially preferably from −10 to 20° C.; and it is preferable to keep the temperature for from 6 to 40 hours. However, since an equilibrium composition is present between the Fries rearrangement compound and the ester compound (2), after a proportion of the Fries rearrangement compound is increased while keeping the reaction system at a temperature in the vicinity of 20° C. for from 1 to 3 hours, the reaction system is cooled to about 0° C. and kept for from 8 to 10 hours, whereby the proportion of the naphthol compound (1) as the Fries rearrangement compound can be further increased.

The reaction mode of the foregoing first to third stages is not particularly limited, and it may be any of a semi-continuous mode or a continuous mode or the like.

In any of the reactions of the first to third stages, a solvent which has ability to dissolve DHDCPD as a raw material therein and which is inert to DHDCPD and HF, for example, a saturated aliphatic hydrocarbon such as hexane, heptane, decane, etc., or the like may be used. In the case of using a solvent, the polymerization reaction is easily suppressed, and the yield is enhanced; however, when an excessive solvent is used, the volume efficiency of the reaction apparatus is lowered, and at the same time, deterioration of a basic unit for energy required for the separation is caused. Therefore, the necessity of use and the use amount are properly chosen. In the case of using a solvent in the first stage, its amount is preferably from 0.5 to 1 time by mass relative to the total sum of DHDCPD and HF. In the second stage, in the case of using the solvent used in the first stage as it is, it is preferable to add the solvent in an amount of from 0.5 to 1.5 times by mass relative to the 1-naphthol. In the third stage, when the solvent is used in the first and second stages, it is not necessary to further add a solvent.

(Treatment after Completion of the Reaction of the Third Stage)

After distilling off HF from the reaction solution containing the naphthol compound (1) obtained through the first to third stages, by purifying the residue by a usual method such as distillation, etc., the naphthol compound (1) in which a proportion of the naphthol compound (1) is 80% by mole or more relative to the total sum of the ester compound (2) and the naphthol compound (1) can be obtained.

The tricyclodecane skeleton of the naphthol compound (1) includes skeleton isomers of an endo-isomer and an exo-isomer, and the naphthol compound (1) is a mixture of those isomers. A ratio of the endo-isomer to the exo-isomer of the tricyclodecane skeleton is not particularly limited, and at the carbonylation temperature of the first stage of 30° C., the ratio of the endo-isomer to the exo-isomer is from 0.4 to 0.6.

A production method of DHDCPD as the raw material of the first stage is not particularly limited, and DHDCPD can be produced by means of hydrogenation of dicyclopentadiene (hereinafter abbreviated as "DCPD") by a known method disclosed in, for example, JP-A-2003-128593, etc.

EXAMPLES

The present invention is hereunder described in more detail with reference to the following Examples, but it should not be construed that the present invention is limited to these Examples.

(Mean Value of the Number of Substituted Hydrogen Atoms Per One Naphthalene Ring)

$^1$H-NMR apparatus: Model JNM-AL400 (400 MHz) (manufactured by JEOL Ltd.)

Solvent: $CDCl_3$ (Deutero chloroform)

Internal standard material: Tetramethylsilane

Calculation method of mean value of the number of substituted hydrogen atoms:

The resin was dissolved in the foregoing solvent (deuteron chloroform), and the solution was subjected to $^1$H-NMR measurement. When an integrated value of methyl protons of a dimethylnaphthalene structure in the vicinity of from 2.3 to 3.2 ppm was defined as 6 which is the number of methyl protons, an integrated value of protons directly bonded on the naphthalene ring in the vicinity of from 6.8 to 8.2 ppm was calculated; and a value obtained by subtracting the thus calculated value from 6 which is the number of hydrogen atoms directly bonded on the naphthalene ring of the dimethylnaphthalene structure was defined as a mean value of the number of hydrogen atoms substituted by a reaction for producing a polyfunctional naphthalene formaldehyde resin among the six hydrogen atoms directly bonded on the naphthalene ring (mean value of the number of substituted hydrogen atoms per one naphthalene ring).

<Measurement of Molecular Weight>

A weight average molecular weight (Mw) and a number average molecular weight (Mn) as reduced into polystyrene were determined by means of a gel permeation chromatography (GPC) analysis, and a degree of dispersion (Mw/Mn) was determined.

—Gel Permeation Chromatography (GPC) Measurement—

Apparatus: Model Shodex GPC-101 (manufactured by Showa Denko K.K.)

Column: LF-804×3

Eluent: THF 1 mL/min

Temperature: 40° C.

<Hydroxyl Group Value>

The hydroxyl group value was determined by dissolving 2 g of a modified resin in 20 mL of an acetic anhydride/pyridine mixed solution (volume ratio=1/9) and allowing it to react and titrating a reaction solution thereof with a 1 mole/L sodium hydroxide aqueous solution. A titration end point was confirmed with phenolphthalein as an indicator. Similarly, 20 mL of an acetic anhydride/pyridine mixed solution (volume ratio=1/9) as a blank sample was also titrated, and a hydroxyl group value was calculated from a difference in titer from the blank sample according to the following expression.

Hydroxyl group value=56.1 (mg/mL)×(Difference in titer (mL))×(Sodium hydroxide aqueous solution factor) ÷(Modified resin amount (g))

<Heat Resistance>

Apparatus: TG/DTA6200, manufactured by SII Nano Technology Inc.

Measurement temperature: From 30 to 550° C. (temperature elevation rate: 10° C./min)

At a point when the temperature reached 400° C., a mass loss rate was measured and defined as an index of the heat resistance.

Synthesis Example 1

Synthesis of tricyclo[5.2.1.0$^{2,6}$]deca-3-ene (DHDCPD):

2,000 g of dicyclopentadiene (DCPD) (manufactured by Maruzen Petrochemical Co., Ltd., purity: 99%) was allowed to react in the presence of a Cu—Cr hydrogenation catalyst under a hydrogen pressure of 2 MPa at 90° C. for about 5 hours until the absorption of hydrogen was not recognized. After completion of the reaction, the Cu—Cr hydrogenation catalyst was removed by means of filtration, and the residue was then purified by means of distillation, thereby obtaining 1,850 g of DHDCPD (purity: 98.5%).

Example 1

Production of Naphthol Compound (1)
(First Stage: Production of Acyl Fluoride (3))

An experiment was carried out using a stainless steel-made autoclave having an internal volume of 500 mL and equipped with a knuck drive type stirrer, three inlet nozzles at an upper part thereof and one drawing nozzle at a bottom thereof, in which an internal temperature could be controlled by a jacket.

First of all, after the inside of the autoclave was purged with carbon monoxide, 189 g (9.4 moles) of hydrogen fluoride was introduced thereinto, and a liquid temperature was controlled to 30° C., followed by elevating a pressure up to 2 MPa with carbon monoxide.

236 g of an n-heptane solution having 141.1 g (1.05 moles) of DHDCPD dissolved therein was fed from the upper part of the autoclave while keeping a reaction temperature at 30° C. and keeping a reaction pressure at 2 MPa, thereby achieving a carbonylation reaction. After completion of feed of DHDCPD, the stirring was continued for about 10 minutes until absorption of carbon monoxide was not recognized.

The formation of the acyl fluoride (3) was confirmed by the presence of a corresponding ethyl ester. A part of the obtained reaction solution was sampled in cooled ethanol, to which was then added water, thereby separating an oily phase and an aqueous phase from each other. After neutralizing the oily phase and washing it with water, the resulting oily phase was analyzed by means of gas chromatography. As a result, a major product was found to be ethyl exo-tricyclo[5.2.1.0$^{2,6}$]decane-2-carboxylate and ethyl endo-tricyclo[5.2.1.0$^{2,6}$]decane-2-carboxylate, with an endo-isomer/exo-isomer ratio being 0.53.

(Second Stage: Production of Ester Compound (2))

Subsequently, 83.4 g (0.58 moles) of 1-naphthol and 83.4 g of n-heptane were introduced into a stainless steel-made autoclave having an internal volume of one liter and equipped with a knuck drive type stirrer, three inlet nozzles at an upper part thereof and one drawing nozzle at a bottom thereof, in which an internal temperature could be controlled by a jacket. After cooling to 0° C., the previously synthesized acyl fluoride-containing carbonylation reaction solution was added with stirring through pipe connection, thereby achieving an esterification reaction.

Apart of the obtained reaction solution was sampled into ice water, thereby separating an oily phase and an aqueous phase from each other. After neutralizing the oily phase and washing it with water, the resulting oily phase was analyzed by means of gas chromatography. As a result, a total purity of the ester compound (2) and the naphthol compound (1) as a Fries rearrangement compound (ester compound (2)/naphthol compound (1)=95.7/4.3) was found to be 75.1%

Also, a desired component was isolated by means of rectification using a rectifying column (theoretical number of plates: 20 plates) and analyzed by means of GC-MS. As a result, a molecular weight of the ester compound (2) was found to be 306. Results of the $^1$H-NMR measurement of the ester compound (2) are shown below.

(Results of $^1$H-NMR Measurement of Ester Compound (2))

$^1$H-NMR (400 MHz, CDCl$_3$, TMS, ppm) δ: 1.24 (m, 3H), 1.50 (m, 2H), 1.70 (m, 5H), 2.09 (m, 2H), 2.55 (m, 2H), 2.65 (m, 1H), 7.25 (d, 1H), 7.46 (t, 1H), 7.50 (m, 2H), 7.71 (d, 1H), 7.86 (m, 1H), 7.92 (m, 1H)

(Third Stage: Production of Naphthol Compound (1))

Subsequently, the temperature of the reaction solution obtained in the second stage was elevated to 20° C., and a Fries rearrangement reaction was carried out at that temperature for 2 hours.

A part of the obtained reaction solution was sampled in ice water, thereby separating an oily phase and an aqueous phase from each other. Thereafter, the oily phase was washed with 100 mL of a 2% by mass sodium hydroxide aqueous solution twice and 100 mL of distilled water twice, followed by dehydration over 10 g of anhydrous sodium sulfate. The obtained oily phase was analyzed by means of gas chromatography. As a result, a total purity of the naphthol compound (1) as a Fries rearrangement compound and the ester compound (2) (naphthol compound (1)/ester compound (2)/=72.2/27.8) was found to be 70.9%.

Furthermore, the reaction solution was cooled to a temperature of 0° C., and this temperature was kept for 8 hours, thereby advancing a Fries rearrangement reaction.

The reaction solution was drawn out from the bottom of the autoclave into ice water, thereby separating an oily phase and an aqueous phase from each other. Thereafter, the oily phase was washed with 100 mL of a 2% by mass sodium hydroxide aqueous solution twice and 100 mL of distilled water twice, followed by dehydration over 10 g of anhydrous sodium sulfate. The obtained oily phase was analyzed by means of gas chromatography. As a result, there were obtained reaction results in which a total purity of the naphthol compound (1) as a Fries rearrangement compound and the ester compound (2) (naphthol compound (1)/ester compound (2)/=81.3/18.7) was 73.8%.

(Distillation)

Simple Distillation:

The obtained solution was subjected to simple distillation. As a result, there was obtained, as a major distillate, 142.1 g (yield: 40.7% based on DHDCPD) of a product having a total purity of the naphthol compound (1) as a Fries rearrangement compound and the ester compound (2) (naphthol compound (1)/ester compound (2)/=80.8/19.2) of 92.4%. Fluctuation in a Fries rearrangement compound/ester ratio to be caused due to the distillation was not observed.

Rectifying Distillation:

Furthermore, a desired component was isolated by means of rectification using a rectifying column (theoretical number of plates: 20 plates) and analyzed by means of GC-MS. As a result, a molecular weight of the desired Fries rearrangement compound was found to be 306. Results of the $^1$H-NMR measurement of the naphthol compound (1) are shown below.

(Results of $^1$H-NMR Measurement of Naphthol Compound (1))

$^1$H-NMR (400 MHz, CDCl$_3$, TMS, ppm) δ: 0.91 (m, 1H), 1.21 (m, 4H), 1.30 (m, 1H), 1.49 (m, 1H), 1.66 (m, 1H), 1.78 (m, 2H), 2.06 (d, 2H), 2.45 (q, 1H), 2.85 (d, 1H), 2.99 (t, 1H), 7.23 (d, 1H), 7.51 (t, 1H), 7.61 (t, 1H), 7.74 (d, 1H), 7.93 (d, 1H), 8.48 (d, 1H), 14.53 (s, 1H)

Production Example 1

Production of Polyfunctional Dimethylnaphthalene Formaldehyde Resin

In a bottom-removal four-necked flask having an internal volume of 2 liters and equipped with a Dimroth condenser, a thermometer and a stirring blade, 218 g of 1,5-dimethylnaphthalene (1.4 moles, manufactured by Mitsubishi Gas Chemical Company, Inc.), 420 g (5.6 moles as formaldehyde) of a 40% by mass formalin aqueous solution (manufactured by Mitsubishi Gas Chemical Company, Inc.) and 194 g of 98% by mass sulfuric acid (manufactured by Kanto Chemical Co., Inc.) were charged, and the mixture was allowed to react for 7 hours in a nitrogen gas stream at atmospheric pressure while refluxing at 100° C. 360 g of ethylbenzene was added as a diluting solvent, and after allowing the mixture to stand, an aqueous phase as a lower phase was removed. Furthermore, after neutralization and washing with water, the ethylbenzene and unreacted 1,5-dimethylnaphthalene were distilled off in vacuo, thereby obtaining 250 g of a 1,5-dimethylnaphthalene formaldehyde resin (hereinafter sometimes referred to as "resin A") which is a pale brown solid.

As a result of the GPC measurement, the resin had Mn of 550, Mw of 1,130 and Mw/Mn of 2.05. The obtained resin was found to have a mean value of the number of substituted hydrogen atoms per one naphthalene ring of 2.6.

Production Example 2

Production of Monomethylnaphthalene Formaldehyde Resin

In a bottom-removal separable flask having an internal volume of one liter and equipped with a Dimroth condenser, a thermometer and a stirring blade, 142.2 g (1.0 mole) of 1-methylnaphthalene (manufactured by Wako Pure Chemical Industries, Ltd., content of sulfur atom: 2,200 ppm, content of nitrogen atom: 3.9 ppm), 150.0 g (2.0 moles as formaldehyde) of a 40% by mass formalin aqueous solution (manufactured by Mitsubishi Gas Chemical Company, Inc.) and 51.4 g of 98% by mass sulfuric acid (manufactured by Kanto Chemical Co., Inc.) were charged, and the mixture was allowed to react for 5 hours in a nitrogen gas stream at atmospheric pressure while refluxing at 100° C. 160 g of ethylbenzene was added as a diluting solvent, and after allowing the mixture to stand, an aqueous phase as a lower phase was removed. Furthermore, after neutralization and washing with water, the ethylbenzene and unreacted 1-methylnaphthalene were distilled off in vacuo, thereby obtaining 150 g of a 1-methylnaphthalene formaldehyde resin (hereinafter sometimes referred to as "resin B") which is a viscous liquid at ordinary temperature.

As a result of the GPC measurement, the resin had Mn of 376, Mw of 405 and Mw/Mn of 1.08. The obtained resin was measured by means of $^1$H-NMR. As a result, the resin was found to have a mean value of the number of substituted hydrogen atoms per one naphthalene ring of 1.4.

Example 2

In a four-necked flask having an internal volume of 0.5 liters and equipped with a Dimroth condenser, a thermometer and a stirring blade, 90 g of the resin A obtained in Production Example 1, 71.1 g (0.49 moles) of 1-naphthol and 0.36 g of p-toluenesulfonic acid were added in a nitrogen gas stream, the temperature was elevated to 185° C., and the mixture was allowed to react for 4 hours. After diluting with a solvent, neutralization and washing with water were carried out, and desolvation and removal of 1-naphthol were carried out in vacuo, thereby obtaining 160 g of a pale brown solid.

As a result of the GPC analysis, the solid had Mn of 848, Mw of 1,630 and Mw/Mn of 1.93 and also had a hydroxyl group value of 175 mg-KOH/g. Results of the evaluation of heat resistance of the obtained modified resin are shown in Table 1.

Example 3

The experiment was carried out in the same manner as in Example 2, except that the charge amount of the 1-naphthol in Example 2 was changed to 38.6 g (0.27 moles), thereby obtaining 130 g of a pale brown solid.

As a result of the GPC analysis, the solid had Mn of 823, Mw of 2,640 and Mw/Mn of 3.21 and also had a hydroxyl group value of 96 mg-KOH/g. Results of the evaluation of heat resistance of the obtained modified resin are shown in Table 1.

Example 4

The experiment was carried out in the same manner as in Example 2, except that 72.5 g (0.25 moles) of the naphthol compound (1) obtained in Example 1 was used in place of 71.1 g (0.49 moles) of the 1-naphthol in Example 2 and that the addition amount of the p-toluenesulfonic acid was changed to 0.22 g, thereby obtaining 142 g of a pale brown solid.

As a result of the GPC analysis, the solid had Mn of 688, Mw of 2,304 and Mw/Mn of 3.35 and also had a hydroxyl group value of 47 mg-KOH/g. Results of the evaluation of heat resistance of the obtained modified resin are shown in Table 1.

Example 5

The experiment was carried out in the same manner as in Example 2, except that 27.5 g (0.1 moles) of the naphthol compound (1) obtained in Example 1 was used in place of 71.1 g (0.49 moles) of the 1-naphthol in Example 2 and that the addition amount of the p-toluenesulfonic acid was changed to 0.22 g, thereby obtaining 98 g of a pale brown solid.

As a result of the GPC analysis, the solid had Mn of 787, Mw of 4,601 and Mw/Mn of 5.85 and also had a hydroxyl group value of 23 mg-KOH/g. Results of the evaluation of heat resistance of the obtained modified resin are shown in Table 1.

Example 6

The experiment was carried out in the same manner as in Example 2, except that 13.3 g (0.05 moles) of the naphthol compound (1) obtained in Example 1 was used in place of 71.1 g (0.49 moles) of the 1-naphthol in Example 2 and that the addition amount of the p-toluenesulfonic acid was changed to 0.22 g, thereby obtaining 88 g of a pale brown solid.

As a result of the GPC analysis, the solid had Mn of 711, Mw of 3,240 and Mw/Mn of 4.56 and also had a hydroxyl group value of 14 mg-KOH/g. Results of the evaluation of heat resistance of the obtained modified resin are shown in Table 1.

Example 7

The experiment was carried out in the same manner as in Example 2, except that 1-naphthol (36 g, 0.25 moles) and the naphthol compound (1) (36 g, 0.12 moles) obtained in Example 1 were used in place of 71.1 g (0.49 moles) of the 1-naphthol in Example 2 and that the addition amount of the p-toluenesulfonic acid was changed to 0.22 g, thereby obtaining 92 g of a pale brown solid.

As a result of the GPC analysis, the solid had Mn of 911, Mw of 8,100 and Mw/Mn of 8.9 and also had a hydroxyl group value of 67 mg-KOH/g. Results of the evaluation of heat resistance of the obtained modified resin are shown in Table 1.

Comparative Example 1

The experiment was carried out in the same manner as in Example 2, except that 94.1 g (1.0 mole) of phenol was used in place of 71.1 g (0.49 moles) of the 1-naphthol in Example 2, thereby obtaining 130 g of a pale brown solid.

As a result of the GPC measurement, the solid had Mn of 678, Mw of 1,130 and Mw/Mn of 1.66 and also had a hydroxyl group value of 253 mg-KOH/g. Results of the evaluation of heat resistance of the obtained modified resin are shown in Table 1.

Comparative Example 2

The experiment was carried out in the same manner as in Example 2, except that 149 g of the resin B obtained in Production Example 2 was used in place of 90 g of the resin A in Example 2, thereby obtaining 220 g of a pale brown solid.

As a result of the GPC analysis, the solid had Mn of 531, Mw of 627 and Mw/Mn of 1.18 and also had a hydroxyl group value of 107 mg-KOH/g. Results of the evaluation of heat resistance of the obtained modified resin are shown in Table 1.

TABLE 1

|  |  | Example 2 | Example 3 | Example 4 | Example 5 | Example 6 | Example 7 | Comparative Example 1 | Comparative Example 2 |
|---|---|---|---|---|---|---|---|---|---|
| Naphthalene formaldehyde resin (g) | | Resin A 90 | Resin A 90 | Resin A 90 | Resin A 90 | Resin A 90 | Resin A 90 | Resin A 90 | Resin B 149 |
| Modifying agent (g) | 1-Naphthol | 71.1 | 38.6 | — | — | — | 36 | — | 71.1 |
| | Naphthol compound (1) | — | — | 72.5 | 27.5 | 13.3 | 36 | — | — |
| | Phenol | — | — | — | — | — | — | 94.1 | — |
| Heat mass loss rate (heat resistance) | | 19 | 23 | 17 | 20 | 22 | 21 | 33 | 46 |

It is understood from Table 1 that a modified resin obtained by subjecting a polyfunctional dimethylnaphthalene formaldehyde resin (resin A) to modification with a naphthol is more excellent in heat resistance than a polyfunctional dimethylnaphthalene formaldehyde resin having been subjected to modification with only a phenol.

On the other hand, in a monomethylnaphthalene formaldehyde resin (resin 2), even when modification with a naphthol was applied, the thermal mass loss was large, and the heat resistance was low.

INDUSTRIAL APPLICATION

The modified dimethylnaphthalene formaldehyde resin of the present invention can be utilizing for widespread applications such as an electrical insulating material, a resin for resist, a semiconductor sealing resin, an adhesive for printed wiring board, a matrix resin for electrical laminate or prepreg to be mounted in electrical instruments, electronic instruments, industrial instruments, etc., a buildup laminate material, a resin for fiber-reinforced plastic, a sealing resin for liquid crystal display panel, a paint, a variety of coating agents, an adhesive and the like.

The invention claimed is:

1. A modified dimethylnaphthalene formaldehyde resin obtained by a process comprising modifying a polyfunctional dimethylnaphthalene formaldehyde resin comprising a constituent unit represented by formula [1] in a molecule thereof with at least one selected from the group consisting of a phenol represented by formula [2], a naphthol represented by formula [3] and a naphthol represented by formula [4]:

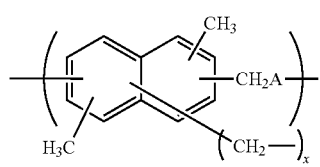

[1]

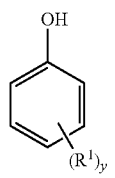

[2]

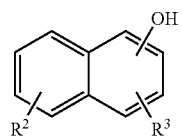

[3]

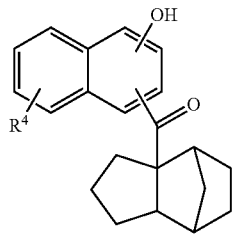

[4]

wherein
at least one of the naphthol represented by formula [3] and the naphthol represented by [4] is included; and
$R^1$ represents an alkyl group comprising from 1 to 4 carbon atoms; each of $R^2$, $R^3$ and $R^4$ independently represents a hydrogen atom or an alkyl group comprising from 1 to 3 carbon atoms; A is represented by $—(OCH_2)_t—$; t is from 0 to 2; x is from 0 to 4; and y represents an integer of from 0 to 2,
wherein the polyfunctional dimethylnaphthalene formaldehyde resin is obtained through a condensation reaction between a dimethylnaphthalene and formaldehyde, a molar ratio of the dimethylnaphthalene to formaldehyde is from 1/2.5 to 1/6, and in the polyfunctional dimethylnaphthalene formaldehyde resin comprising a constituent unit represented by formula [1] in a molecule thereof, a mean value of the number of hydrogen atoms substituted by a reaction producing the dimethylnaphthalene formaldehyde resin, among the six hydrogen atoms directly bonded on a naphthalene ring, is from 1.5 to 3.5.

2. The modified dimethylnaphthalene formaldehyde resin according to claim 1, wherein a dimethylnaphthalene which is a raw material of the polyfunctional dimethylnaphthalene formaldehyde resin comprising a constituent unit represented by formula [1] in a molecule thereof, is at least one member selected from the group consisting of 1,5-dimethylnaphthalene, 1,6-dimethylnaphthalene, 2,6-dimethylnaphthalene, 1,7-dimethylnaphthalene, 1,8-dimethylnaphthalene, and 2,7-dimethylnaphthalene.

3. The modified dimethylnaphthalene formaldehyde resin according to claim 2, wherein the dimethylnaphthalene is a dimethylnaphthalene obtained by a chemical synthesis, wherein starting raw materials for the chemical synthesis comprise o-xylene and 1,3-butadiene, or p-xylene and 1,3-butadiene.

4. The modified dimethylnaphthalene formaldehyde resin according to claim 1, wherein the phenol represented by formula [2] is at least one selected from the group consisting of phenol, cresol, 4-t-butylphenol, and xylenol.

5. The modified dimethylnaphthalene formaldehyde resin according to claim 1, wherein the naphthol represented by formula [3] is 1-naphthol and/or 2-naphthol.

6. The modified dimethylnaphthalene formaldehyde resin according to claim 1, wherein the naphthol represented by formula [4] is:

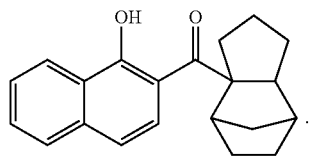 [SMILES: O=C(c1ccc2ccccc2c1O)C12CCCC1C1CCC2C1]

7. The modified dimethylnaphthalene formaldehyde resin according to claim 1, having a weight average molecular weight (Mw) of from 500 to 5,000.

* * * * *